(12) United States Patent
Tomko et al.

(10) Patent No.: US 6,630,539 B1
(45) Date of Patent: Oct. 7, 2003

(54) NEOPENTYLENE 1-PHENYLVINYL PHOSPHONATE

(75) Inventors: John Tomko, Dobbs Ferry, NY (US); Jeffrey E. Telschow, Tarrytown, NY (US)

(73) Assignee: AKZO Nobel N.V., Arnhem (NL)

( * ) Notice: Subject to any disclaimer, the term of this patent is extended or adjusted under 35 U.S.C. 154(b) by 0 days.

(21) Appl. No.: 08/386,393

(22) Filed: Feb. 10, 1995

(51) Int. Cl.[7] .............................................. C08F 267/04
(52) U.S. Cl. ..................................................... 525/285
(58) Field of Search ................. 525/285, 240; 524/10, 340

(56) References Cited

U.S. PATENT DOCUMENTS

| | | | |
|---|---|---|---|
| 4,255,324 A | * | 3/1981 | Granzow et al. ............ 525/285 |
| 5,310,808 A | | 5/1994 | Grey .......................... 525/287 |

OTHER PUBLICATIONS

White, "Chemical Patent Practice", (1991), pp. 144–147.*
Edmundson, R.S. Cyclic organophosphorus compounds. Part XVI mass spectrometric fragmentation of some 5,5–dimethyl–1,3,2–dioxaphosphorinan 2–oxides and 2–sulphides. (1981) Phosphorus and Sulfur. vol. 9, pp. 307–314.*

* cited by examiner

*Primary Examiner*—Marjorie Moran
(74) *Attorney, Agent, or Firm*—Richard P. Fennelly

(57) ABSTRACT

Compounds of the formula

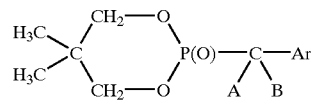

wherein the compound is neopentylene 1-phenylvinyl-phosphonate.

1 Claim, No Drawings

NEOPENTYLENE 1-PHENYLVINYL PHOSPHONATE

BACKGROUND OF THE INVENTION

U.S. Pat. No. 5,310,808 to R. A. Grey describes various vinyl phosphonate derivatives which are useful in the manufacture of flame retarded thermoplastic copolymers. Various aryl group-containing vinylphosphonate species are embraced by a formula depicted at col. 3, lines 14–26 of this patent in which a linear or branched divalent hydrocarbyl radical, B, is depicted as being bonded at either end thereof to the two oxygen atoms of the moiety

with the structures —$CH_2$—$CH_2$— and —$CH(CH_3)$—$CH_2$— being given as examples of preferred groups for B.

SUMMARY OF THE INVENTION

The present invention are certain novel neopentylene phosphonate compounds containing, as the type of divalent group B shown in both the compounds of U.S. Pat. No. 5,310,808 and intermediates thereof, the novel divalent linkage —$CH_2$—$C(CH_3)_2$—$CH_2$—.

DESCRIPTION OF PREFERRED EMBODIMENTS

The compounds of the present invention are, for example, embraced by the formula

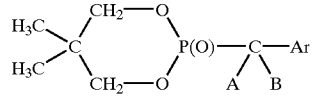

where: Ar is substituted or unsubstituted phenyl;
  A is selected from the group consisting of hydrogen and, if conjoint with B, $CH_2$; and
  B is selected from the group consisting of hydroxy, oxyacyl, and, if conjoint with A, $CH_2$. It will be appreciated that having A and B conjoint as $CH_2$ makes the entire grouping C<A(B) a vinyl group.

A particularly preferred embodiment of the present invention relates to final compounds where the group C<A(B) does form a vinyl structure having A and B being conjoint as the moiety $CH_2$. This type of compound class is exemplified by the compound neopentylene 1-phenylvinylphosphonate which has the formula:

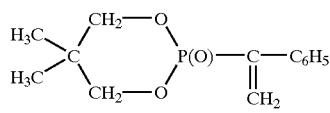

Another embodiment of the present invention is exemplified by the class of novel intermediates for the previously described vinyl group-containing compound. One specific compound of this type is neopentylene 1-acetoxy-1-phenylethylphosphonate which is of the formula:

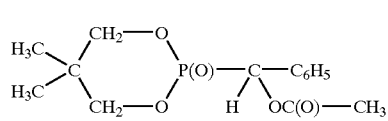

Yet another embodiment of the present invention is the novel intermediate compounds for the previously described 1-acetoxy containing compounds. These compounds are exemplified by the compound neopentylene 1-hydroxy-1-phenylethylphosphonate which is of the formula:

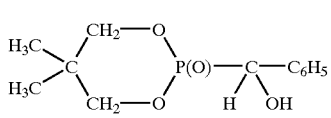

The process for forming the desired final products of the type exemplified by (I) involves the reaction of neopentylene hydrogen phosphonate with acetophenone to yield compounds as exemplified by (III) followed by acetylation with acetic anhydride to form the type of compound exemplified by (II) followed by acid-catalyzed deacetylation of (II) to form the final desired compound (I).

EXAMPLE 1

This Example illustrates the synthesis of neopentylene 1-hydroxy-1-phenylethylphosphonate.

Neopentylene hydrogenphosphonate (16.0 gm, 0.107 mole), acetophenone (12.8 gm, 0.107 mole), and 16 gm of V&MP Naphtha were placed into a 100 cc nitrogen-blanketed flask. Then, 1,1,3,3-tetramethylguanidine (0.74 gm) was added at 30° C. to 50° C. in several aliquots over a period of eight hours and forty-five minutes. Crystals of the desired hydroxy adduct formed as the reaction proceeded and another 26.5 additional grams of V&MP Naphtha were added to make the slurry stirrable. The reaction mixture was then filtered, and the solid was washed two times with hexane. The yield of crystals was 90.3%, they had a melting point of 157° C. to 161.5° C., a purity of 95.2% by $^{31}P$ nmr, and δ 16.0 $d_6$-DMSO.

EXAMPLE 2

This Example shows the synthesis of neopentylene 1-acetoxy-1-phenethylphosphonate.

Initially, neopentylene 1-hydroxy-1-phenylethylphosphonate, from Example 1 (10.0 gm, 0.037 mole) and acetic anhydride (32 gm, 0.313 mole) were placed into a nitrogen blanketed reaction flask. The slurry was then vigorously stirred, and 5.4 gm of strongly acidic ion exchange resin (AMBERLYST 15 brand from Rohm & Haas Co.) were added in a single aliquot. The initially exothermic reaction (maximum temperature of 43° C.) was then allowed to cool and stand overnight. Assay of the neopentylene 1-acetoxy-1-phenylethylphosphonate in the final mixture was 88.1% by $^{31}P$ nmr and δ 10.7 $d_6$-DMSO.

EXAMPLE 3

This Example illustrates synthesis of neopentylene 1-phenylvinylphosphonate.

The crude reaction mixture from Example 2 was stirred and heated for thirty minutes at 79° C. to 90° C. The resulting slurry contained 86.9% of the desired neopentylene 1-phenylvinylphosphonate by $^{31}P$ nmr analysis. The final slurry was washed two times with 15 gm of water and filtered. The yield of air dried crystals was 75.8%, 99% purity by $^{31}P$ nmr, and δ 10.4 $d_6$-DMSO.

We claim:
1. Neopentylene 1-phenylvinylphosphonate.

* * * * *